(12) United States Patent
Lerín Martínez et al.

(10) Patent No.: US 11,464,754 B2
(45) Date of Patent: Oct. 11, 2022

(54) BETAINE FOR THE PREVENTION OF OBESITY

(71) Applicant: HOSPITAL SANT JOAN DE DEU, Esplugues de Llobregat (ES)

(72) Inventors: Carlos Lerín Martínez, Esplugues de Llobregat (ES); José Carlos Jiménez Chillarón, Esplugues de Llobregat (ES); Marta Ramón Krauel, Esplugues de Llobregat (ES)

(73) Assignee: HOSPITAL SANT JOAN DE DEU, Esplugues de Llobregat (ES)

( * ) Notice: Subject to any disclaimer, the term of this patent is extended or adjusted under 35 U.S.C. 154(b) by 229 days.

(21) Appl. No.: 16/612,806

(22) PCT Filed: May 11, 2018

(86) PCT No.: PCT/EP2018/062203
§ 371 (c)(1),
(2) Date: Nov. 12, 2019

(87) PCT Pub. No.: WO2018/206763
PCT Pub. Date: Nov. 15, 2018

(65) Prior Publication Data
US 2020/0147027 A1 May 14, 2020

(30) Foreign Application Priority Data
May 12, 2017 (EP) .................................. 17382270

(51) Int. Cl.
| | | |
|---|---|---|
| *A61K 31/205* | (2006.01) | |
| *A61P 3/04* | (2006.01) | |
| *A61K 31/401* | (2006.01) | |
| *A61K 31/405* | (2006.01) | |
| *A61K 33/36* | (2006.01) | |
| *A61K 35/20* | (2006.01) | |

(52) U.S. Cl.
CPC .......... *A61K 31/205* (2013.01); *A61K 31/401* (2013.01); *A61K 31/405* (2013.01); *A61K 33/36* (2013.01); *A61K 35/20* (2013.01); *A61P 3/04* (2018.01)

(58) Field of Classification Search
CPC .......... A61K 31/205; A61K 33/36; A61P 3/04
See application file for complete search history.

(56) References Cited

U.S. PATENT DOCUMENTS

| | | | | |
|---|---|---|---|---|
| 6,613,367 B1 * | 9/2003 | Wells | ...................... | A23L 33/16 426/72 |
| 2006/0078629 A1 * | 4/2006 | Serfontein | .............. | A23L 33/15 424/702 |
| 2008/0031964 A1 | 2/2008 | Messadek | | |
| 2014/0050810 A1 | 2/2014 | Bok et al. | | |

FOREIGN PATENT DOCUMENTS

| | | | | |
|---|---|---|---|---|
| CN | 101322698 A | * | 12/2008 | ........... A61K 31/205 |
| CN | 101322698 A | | 12/2008 | |
| EP | 2143341 A1 | | 1/2010 | |
| FR | 2710245 A1 | | 3/1995 | |
| WO | WO 2007/107319 A1 | | 9/2007 | |

OTHER PUBLICATIONS

English machine translation of CN-101322698-A dated Nov. 15, 2021. (Year: 2021).*
M. Inoue-Choi, et al., "One-carbon metabolism nutrient status and plasma s-adenosylmethionine concentrations in middle-aged and older chinese in singapore," Int J Mol Epidemiol Genet., 2012, v.3, pp. 160-173.
E. Arning, et al., "Quantitation of 5-methyltetrahydrofolate in cerebrospinal fluid using liquid chromatography-electrospray tandem mass spectrometry," Methods Mol. Biol., 1378, 175-182 (2016).
N. Segata, et al,, "Metagenomic biomarker discovery and explanation," Genome Biol 12, R60 (2011).
Linde Van Lee et al.: "Prospective 1-5 Associations of Maternal Betaine Status With Offspring Weitht and Body Composition at Birth: The Gusto Cohort Study", American Journal of Clinical Nutrition, Sep. 21, 2016 (Sep. 21, 2016), pp. 1-7.
Kim, et al., "Molecular mechanism of Betaine on hepatic lipid metabolism: Inhibition of Forkhead Box 01 (FoxOl) binding to Peroxisome Proliferator-Activated Receptor Gamma (PPARy)", Journal of Agriculture and Food Chemistry; Aug. 21, 2016; vol. 64; pp. 6819-6825.
Luan, et al., "Hypaphorine, an Indole Alkaloid isolated from Caragana korshinskii KOM., Inhibites 3T3-LI Adipocyte Differentiation and improves insulin sensitivity in Vitro", Chemistry & Biodiversity; Apr. 11, 2017; vol. 14(7), el700038.
Randall, et al., "Competitive accumul of betaines by *Escherichia coli* K-12 and derivative strains lacking betaine porters", Biochimica et Biophysica Acta 1995; vol. 1245, pp. 116-120.

(Continued)

*Primary Examiner* — Michael B. Pallay
(74) *Attorney, Agent, or Firm* — Squire Patton Boggs (US) LLP

(57) ABSTRACT

The present invention provides a betaine compound for use in the prevention of obesity, excessive fat accumulation and/or metabolic disorders associated with either of the foregoing in a subject, wherein the prevention comprises administering the betaine compound directly to the subject during infancy or, alternatively, to the subject's mother during breast-feeding. Also provided are compositions comprising an effective amount of betaine compound together with one or more pharmaceutically or edible acceptable excipients and/or carriers for this use.

19 Claims, 7 Drawing Sheets
Specification includes a Sequence Listing.

(56) References Cited

OTHER PUBLICATIONS

Kawakami, et al., "Effects of Dietary supplementation with Betaine on nonalcoholic Steatohepatitis (NASH) Mouse Model", J. Nutra Sci Vitaminol 2012; vol. 58; pp. 371-375.

Xu, et al., "Betaine alleviates hepatic lipid accumulation via enhancing hepatic lipid export and fatty acid oxidation in rats fed with high-fat diet", British Journal of Nutrition; Apr. 29, 2015; vol. 113, pp. 1835-1843.

\* cited by examiner

BETAINE FOR THE PREVENTION OF OBESITY

CROSS-REFERENCE TO RELATED APPLICATIONS

This application is a U.S. national stage application filed under 35 U.S.C. 371 of International Patent Application No. PCT/EP2018/062203, filed on May 11, 2018, which claims the benefit of European Patent Application EP17382270.1 filed on May 12, 2017, all of which are incorporated herein by reference in their entirety.

TECHNICAL FIELD

The present invention relates to the field of nutrition and disease, more particularly to the prevention and treatment of obesity and related diseases.

BACKGROUND ART

Obesity is widely recognized as a chronic disease associated with many serious health problems including type 2 diabetes, cardiovascular disease, hypertension, and at least a dozen types of cancer. In the past three decades, the prevalence of obesity and overweight has risen substantially and affects over 600 million people globally. Authorities worldwide view it as one of the most serious public health problems of the 21st century.

Excessive weight gain is influenced by a wide range of factors including genetic predisposition, improper nutrition, individual behavior, as well as environmental and social factors. The role of dietary nutrients in obesity has been long debated and numerous studies have been performed to find compounds useful in the prevention and treatment of obesity, with limited success. Despite intensive research on therapeutics and dietary supplements, the gold standard for the prevention and treatment of obesity is dieting and physical exercise. However, diet programs usually produce weight loss over the short term, but maintaining this weight loss is difficult, often requiring continuous exercise and a permanent lower food energy diet. Non-compliance with this regime and subsequent gain weight is particularly high in obese and overweight population.

Surgical interventions are effective for the treatment of obesity and are routinely performed in some countries in severe obese patients. The types of procedures include laparoscopic adjustable gastric banding, Roux-en-Y gastric bypass, vertical-sleeve gastrectomy, and biliopancreatic diversion. Surgery for severe obesity is associated with long-term weight loss, improvement in obesity related conditions, and decreased overall mortality. However, associated costs to public health are high and complications occur in about 17% of cases (reoperation is needed in 7% of cases). Due to its cost and risks, researchers are searching for other effective yet less invasive treatments for this condition.

Childhood obesity has been steadily increasing in developed countries and has become a mayor public concern. Governments worldwide design strategic plans and launch official publicity programs to raise awareness on this issue. But childhood obesity is not easily dealt with, since constant dieting is difficult to be observed by children and surgical interventions are not indicated. Great efforts are being made in prevention strategies but these often fail on the face of lifestyle and dietary habits.

It is a general consensus that particular emphasis should be made in prevention strategies for population at risk of developing childhood obesity. Among the risk factors, maternal overweight leads to accelerated growth, and is a major predictor of childhood obesity. This has critical consequences for the obesity epidemic, as childhood overweight is often tracked into adult life leading to an obesogenic cycle that perpetuates obesity and metabolic risk over the next generations. Postnatal nutrition has also been described as playing an important role in determining growth and obesity risk. Compared to breastfeeding, formula use has been consistently associated with childhood overweight, and its composition influences obesity risk. Breastfeeding duration is inversely associated with obesity risk, and differences in milk composition, including oligosaccharide diversity and hormone levels, correlate to infant growth, adiposity, and microbiota composition. However, while some reports have identified alterations in milk composition induced by maternal obesity (higher leptin, insulin, IL-6, TNF-α), these are not linked to infant accelerated weight gain, and have even been suggested to be protective factors. Thus, how specific milk components contribute to mother-to-child transmission of obesity risk is poorly understood.

Due to the high prevalence of obesity and its associated health consequences, effective strategies are needed to reduce the incidence of obesity and, in particular, to put an end to the obesogenic cycle that perpetuates this unhealthy condition over the generations in individuals at risk.

SUMMARY OF INVENTION

The inventors have surprisingly found that administering betaine to infants reduces the incidence of obesity and associated disorders not only while supplementation is performed, but also later in the life of said infants, far after betaine supplementation has been stopped.

This surprising effect is demonstrated in the examples below. As shown in the examples, the inventors have found a strong association between lower milk betaine content and accelerated early growth in infants at risk of obesity. Moreover, maternal supplementation experiments in mice have shown that increased betaine intake during lactation decreased adiposity and improved systemic metabolism throughout adulthood.

Thus, a first aspect of the invention provides a betaine compound for use in the prevention of obesity, excessive fat accumulation and/or metabolic disorders associated with either of the foregoing in a subject, wherein the prevention comprises administering the betaine compound directly to the subject during infancy or, alternatively, to the subject's mother during breast-feeding.

The above aspect may be reformulated as use of a betaine compound for the preparation of a composition for the prevention of obesity, excessive fat accumulation and/or metabolic disorders associated with either of the foregoing in a subject, wherein the prevention comprises administering the betaine compound directly to the subject during infancy or, alternatively, to the subject's mother during breast-feeding. The invention also relates to a method for the prevention of obesity, excessive fat accumulation and/or metabolic disorders associated with either of the foregoing in a subject comprising administering an effective amount of the betaine compound together with pharmaceutically or edible acceptable excipients and/or carriers directly to the subject during infancy or, alternatively, to the subject's mother during breast-feeding.

In a second aspect the invention provides a composition comprising an effective amount of a betaine compound together with one or more pharmaceutically or edible acceptable excipients and/or carriers for use as defined above. The composition may be a pharmaceutical composition (that is, a medicament) or a non-pharmaceutical composition, such as an edible composition, for example a food product or a dietary supplement.

DETAILED DESCRIPTION OF THE INVENTION

Figure 1:
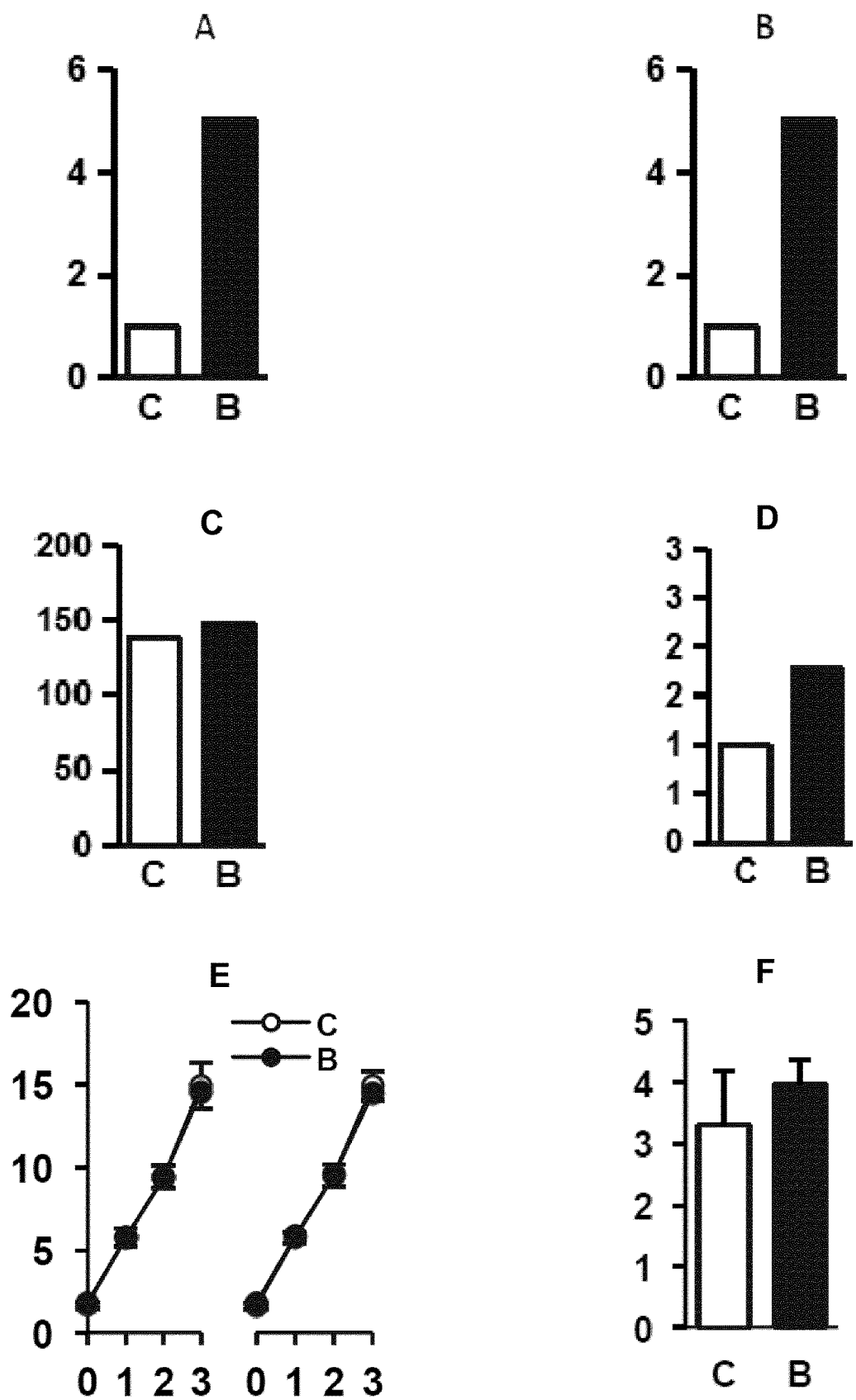
FIG. 1: A) Betaine relative levels in arbitrary units. B) Milk macronutrient composition in g/100 mL (n=5/group); Ch, carbohydrates; Prot, protein. C) Milk energy content in Kcal/mL (n=5/group). D) Plasma betaine levels in arbitrary units in 2-week-old males (n=6/group). E) Offspring body weight during lactation (left graphic represents males, n=18; right graphic represents females, n=12); Y axis represents body weight in g; X axis represents weeks of like. F) Milk intake at 1 week of age expressed in % body weight (n=4 litters/group). Data are mean±sem. *, t-test p<0.05; **, p<0.0001. For all bar figures: white bars represent milk from control dams (n=8), and black bars represent milk from betaine-treated dams (n=8).
Figure 2:
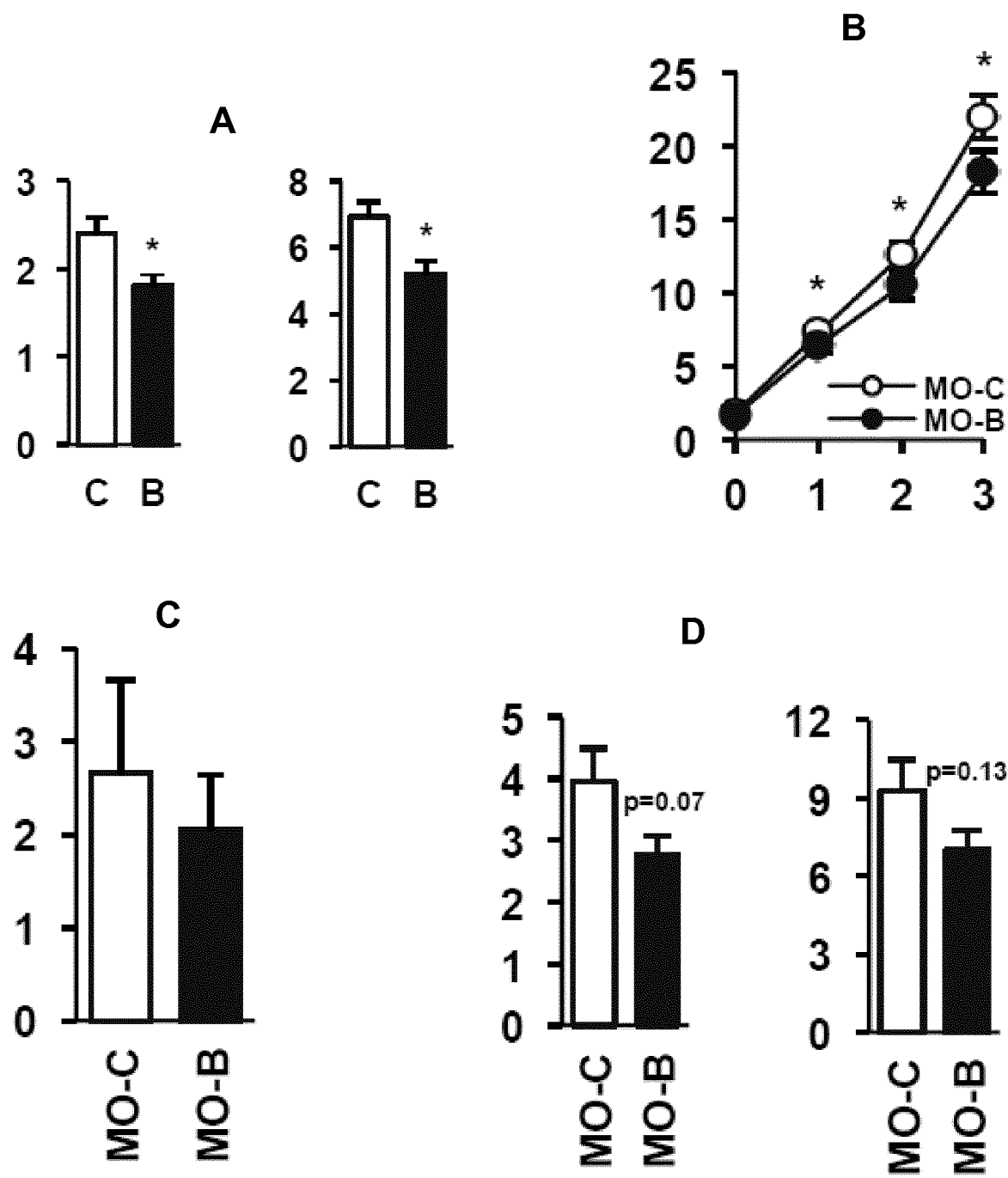
FIG. 2: A) Fat mass expressed g (right) and % (left) in 6-week-old male mice from control (white bars, n=7) or betaine-treated dams (black, n=9). B) Body weight of male offspring from obese control (MO-C, n=19) or betaine-treated (MO-B, n=21) dams; Y axis represents body weight (g); X axis represents weeks of age. C) Milk intake at 1 week of age (n=3 litters/group) expressed as % of body weight. D) Fat mass expressed in g in 6-week-old male mice (n=8/group). Data are mean±sem. *, t-test p<0.05; **, p<0.0001.

The present invention is related to prevention of obesity, excessive fat accumulation and associated disorders by administering a betaine compound to infants.

"Obesity" is a condition in which the natural energy reserve, stored in the fatty tissue of animals, in particular humans and other mammals, is increased to a point where it is associated with certain health conditions or increased mortality. The expression "excessive fat accumulation" is understood as having more body fat than is optimally healthy. "Excessive fat accumulation" may be also termed "overweight". Obesity and excessive fat accumulation are usually defined by the Body mass index of an individual. "Body mass index" or "BMI" means the ratio of weight in kg divided by the height in meters, squared. "Obesity" is generally defined for a human adult as having a BMI greater than 30. "Overweight" is generally considered for human adults as BMI from 25 to 30. For human children above 2 years of age the BMI is plotted on a BMI vs. age growth chart (for either girls or boys) to obtain a percentile ranking. For children below 2 years (infants) what is plotted is the weight-for-length instead of the BMI. Percentiles and z-scores are the most commonly used indicator to assess the size and growth patterns of individual children. The percentile indicates the relative position of the child's BMI or weight-for-length in a population of individuals with the same sex and age. The z-score indicates the number of standard deviations (SDS) that one individual deviates from the mean of a population with the same sex and age. Human children are considered overweight if their BMI or weight-for-length percentile is located between the 85th and 95th percentile, or the z-score between 1 and 2 SDS. Human children are considered obese if their BMI or weight-for-length percentile is located on or above the 95th percentile, or z-score equal or higher than 2 SDS.

The term "undernutrition", also termed as "undernourishment", is understood as lack of adequate nutrition resulting from insufficient food, unbalanced diet, or defective assimilation. Undernourishment can also occur as a result of certain diseases or genetic conditions. Human infants are usually termed as undernourished if their BMI or weight-for-length is located on or below the 10th percentile. Severe undernourished in human infants is usually considered if the BMI or weight-per-length is located on or below the 3th percentile.

Metabolic disorders that are associated with overweight, obesity and/or excessive fat accumulation are well known to skilled artisans. For example, these disorders include cardiovascular diseases such as coronary heart disease; insulin resistance; type 2 diabetes; hypertension; sleep apnoea, respiratory problems and/or dyslipidaemia; but also some cancers such as endometrial, breast, and/or colon cancer; stroke; liver and gallbladder disease; osteoarthritis; and/or gynaecological problems. In particular, embodiments of the invention the metabolic disorders that are associated with obesity and/or excessive fat accumulation are selected from coronary heart disease, insulin resistance, type 2 diabetes, hypertension, dyslipidaemia, and sleep apnoea, more particularly with coronary heart disease, hypertension, dyslipidaemia, and sleep apnoea.

In the sense of the present invention, the term "infancy" is understood as the time period when a subject has an age for which breast feeding is recommended, either as sole feeding means or combined with infant formula and/or solid food. In humans, infancy is usually considered from 0 to around 2 years of age, i.e. from birth to around 2 years of age. The skilled person, however, will understand that the term "infancy", same as the terms "childhood", "adolescence" and "adulthood", is not an absolute term, since it depends on the maturation of each individual. Thus, each of these terms is associated to an average age range, more than to an exact age range.

"Childhood" is understood in the sense of the present invention as the period between infancy and the beginning of puberty. "Puberty" is generally defined as the process of physical changes through which a child's body matures into an adult body capable of sexual reproduction. The terms "puberty" and "adolescence" are used interchangeably. On average for humans, girls begin puberty around ages 10-11; boys around ages 11-12. Thus, for humans, "childhood" expands on average from around 3 to around 12 years of age. "Puberty" expands in humans on average from around 13 to around 18 years of age.

"Adulthood" is generally defined as the period starting from the end of puberty, when the individual is fully growth and sexually mature. In human context, the term adult additionally has meanings associated with social and legal concepts. In the sense of the present invention the term "adulthood" refers preferably to biological adulthood, which in humans starts at around age 18 until death of the individual.

"Prevention" is understood in the sense of avoiding developing obesity, excessive fat accumulation and/or metabolic disorders associated with either of the foregoing, as well as to reducing the likelihood of developing obesity, excessive fat accumulation and/or metabolic disorders associated with either of the foregoing.

In the sense of the present invention "mother" is the female that is breast-feeding the subject as an infant. The mother is usually but not necessarily the female parent of the subject.

"Infection" is understood as the invasion of an organism's body tissues by disease-causing agents (often called pathogens), their multiplication, and the reaction of host tissues to these organisms and the toxins they produce. Infections are the cause of a great number of diseases.

The expression "effective amount" as used herein, refers to the amount of a compound that, when administered, is sufficient to prevent development of, or alleviate to some extent, one or more of the symptoms of the condition which is addressed. The particular dose of compound administered according to this invention will of course be determined by the particular circumstances surrounding the case, including the compound administered, the route of administration, the particular condition being treated, and the similar considerations. When the composition of the invention is a pharmaceutical composition, the "effective amount" is a "therapeutically effective amount".

The expression "pharmaceutically acceptable excipients and/or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. Similarly, the expression "edible acceptable excipients and/or carriers" refers to ingredients, materials, compositions or vehicles that are acceptable for edible compositions, such as food products, nutraceuticals or dietary supplements. "Edible acceptable excipients and/or carriers" must be food grade ingredients. Each component must be edible acceptable in the sense of being compatible with the other ingredients of the edible composition. It must also be suitable for use when ingested without excessive toxicity, irritation, allergic response, immunogenicity or other problems or complications commensurate with a reasonable benefit/risk ratio.

The term "dietary supplement", "food supplement" or "nutritional supplement" or "nutraceutical" as used herein interchangeably refers to a preparation intended to supplement the diet and provide nutrients that may be missing or may not be consumed in sufficient quantity in a person's diet.

"Infant formula" is understood as generally in the art as a manufactured food designed and marketed for feeding to infants and usually prepared for bottle-feeding or cup-feeding from powder (mixed with water) or liquid (with or without additional water).

"Betaine compound" in the sense of the present invention is understood as zwitterionic compounds like glycine betaine (also called N,N,N-trimethylammonioacetate or N,N,N-trimethylglycine) and compounds similar to glycine betaine derived from other amino acids.

In one embodiment, the betaine compound has the formula (I):

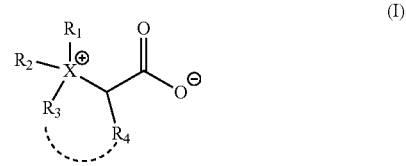

wherein:

X is N or As;

R1 and R2 are independently (C1-C6)alkyl optionally substituted with one or more halogen atoms; and R3 and R4 form a 5- to 6-membered ring together with the atoms to which they are attached that is optionally substituted with one or more substituents selected from OH, halogen, and (C1-C3)alkyl optionally substituted with one or more halogen atoms; or alternatively R3 is (C1-C6)alkyl; and R4 is H or (1H-indol-3-yl)methyl.

The term "(C1-Cn)-alkyl" as used herein refers to a saturated branched or linear hydrocarbon side chain with 1 to n carbon atoms.

In particular embodiments of the invention the betaine compound is selected from glycine betaine, arsenobetaine, proline betaine, 4-hydroxyproline betaine and tryptophan betaine, represented, respectively, by formula II to VI:

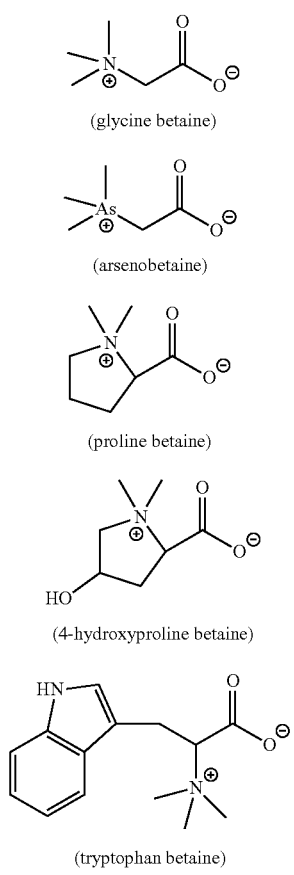

In another particular embodiment, the betaine compound is selected from glycine betaine, arsenobetaine and proline betaine. In yet another embodiment, the betaine compound is glycine betaine.

The present invention finds application in mammals, for veterinary or medicinal fields. The invention is useful in particular in the fields of pet's health, livestock health and human health. Preferably, the present invention finds application in human health. Thus in a preferred embodiment of the first aspect of the invention the betaine compound is for administration to humans.

In preferred embodiments of the first aspect of the invention, the betaine compound is for the prevention of obesity.

Interestingly, the inventors have found lasting beneficial metabolic consequences, including reduced fat accumulation, when administering betaine compound only during infancy. The experimental data strongly indicate that increased betaine compound exposure during early life (infancy) might suffice for lowering adiposity and ameliorating metabolic health later in life. This finding is advantageous for finally providing a long searched strategy for the prevention of obesity and associated disorders, in particular for the prevention of childhood obesity. Therefore, in one embodiment of the present invention the prevention of obesity, excessive fat accumulation and/or metabolic disorders associated with either of the foregoing comprises the prevention after infancy, that is, in the subject's childhood, in the subject's adolescence and/or in the subject's adulthood. In another embodiment the prevention of obesity, excessive fat accumulation and/or metabolic disorders associated with either of the foregoing comprises the prevention starting from 3 years of age, starting from 13 years of age and/or starting from 18 years of age.

Some subjects are at higher risk of developing obesity, excessive fat accumulation and/or metabolic disorders associated with either of the foregoing. Interventions to reduce the likelihood of developing these conditions in such at-risk population are particularly beneficial. Thus, in a particular embodiment of the first aspect of the invention, the subjects are at risk of suffering from obesity, excessive fat accumulation, and/or metabolic disorders associated with either of the foregoing.

Some early-life factors have been clearly associated with overweight, obesity and associated disorders later in life, i.e. during childhood, adolescence and/or adulthood. Among them, maternal obesity and diabetes, foetus undernutrition, excess gestational weight gain, lack of breast-feeding, maternal smoking and rapid infant growth are particularly representative. These risk factors may be due to lifestyle or genetic reasons. Although the association may be modest for each of the risk factors, a large effect may be achieved when acting on a small attributable risk if the risk factor is highly prevalent in a population. Also, some possible determinants may become more important than others because they are easier to be addressed through the implementation of an effective intervention. In a particular embodiment of the first aspect of the invention, the subjects have a condition selected from being born to obese mothers, have suffered intrauterine growth retardation, have low birth-weight (in particular a weight-for-length located on or below the 3th percentile), have rapid weight gain after birth, and combinations thereof.

According to the findings of the inventors, increased betaine intake during lactation decreased adiposity and improved systemic metabolism throughout adulthood. Thus, an effective strategy to prevent obesity, excessive fat accumulation and/or associated disorders may be feeding a betaine compound to the breast-feeding mothers. In a particular embodiment of the first aspect of the invention the betaine compound is administered to the subject's mother while breast-feeding. However, this strategy is not always possible, because some infants are mainly or solely fed on infant formula. Further, formula-fed infants are at higher risk of accelerated growth and obesity. Prevention of obesity by betaine compound administration to these infants is desirable. Thus, in another embodiment of the first aspect of the invention the betaine compound is administered directly to the subject during infancy. Direct administration to the subject during infancy may be achieved, for example, by including betaine compound in infant formula, infant food or dietary supplements for infants. Direct administration to the subjects during infancy may also be in the form of a solution containing the betaine compound and appropriate excipients and/or carriers for oral administration, for example, with a syringe or with a dropper. In another embodiment of the first aspect of the invention the betaine compound is administered to a male human subject during infancy. In another embodiment of the first aspect of the invention the betaine compound is administered to a female human subject during infancy.

The inventors have found that the amount of betaine compound that is needed to obtain the effect of preventing obesity, excessive fat accumulation and/or metabolic disorders associated with either of the foregoing is far above what can be obtained with the natural diet, and is also far above what could be obtained by increasing the ingestion of natural betaine sources. In general, the inventors have found that the amount of betaine compound that needs to be administered directly to the subject during infancy in order to achieve the sought effect may be from 2 to 500 mg/Kg/day, in particular from 4 to 100 mg/Kg/day, more particularly from 4 to 50 mg/Kg/day. Thus, another embodiment of the invention refers to a betaine compound for use as defined above, wherein the prevention and/or treatment comprises administering directly to the subject during infancy from 4 to 100 mg betaine compound/Kg/day. This is also generally termed as "daily dose". When the betaine compound is administered to the subject's mother during breast-feeding, the daily dose to be administered to the mother may be from 500 mg to 20 g per day, in particular from 1 to 10 g/day, more particularly from 2 to 6 g/day. Thus, another embodiment of the invention refers to a betaine compound for use as defined above, wherein the prevention and/or treatment comprises administering from 1 to 10 g betaine compound/day to the subject's mother during breast-feeding.

The present invention contemplates administering the betaine compound as a pure betaine compound, for example, in the form of a powder to be ingested directly or dissolved in liquids. The invention, however, additionally contemplates formulating the betaine compound as composition comprising an effective amount of betaine compound together with other ingredients, such as excipients and/or carriers.

A second aspect of the invention thus provides a composition comprising an effective amount of betaine compound together with one or more pharmaceutically or edible acceptable excipients and/or carriers for use as defined above. The effective amount in the composition can be determined by the skilled person considering the compound administered, daily dose, route of administration, age of the subject, weight of the subject, and other considerations. The composition of the invention can be administered once a day, once a week, several days per week or several times per day.

In one embodiment of the second aspect of the invention, the composition for use as defined above is a pharmaceutical composition and the excipients are pharmaceutically acceptable excipients.

In another embodiment, the composition for use as defined above is a dietary supplement and the excipients are edible acceptable excipients. In particular embodiments, the composition is a dietary supplement for breast-feeding women. In another particular embodiment, the composition is a dietary supplement for infants.

The pharmaceutical compositions and dietary supplements of the invention can be formulated in several forms that include, but are not limited to, solutions, tablets, capsules, granules, suspensions, dispersions, powders, lozenge, chewable candy, candy bar, concentrate, drops, elixir, emulsion, film, gel, granule, chewing gum, jelly, oil, paste, pastille, pellet, syrup, chewable gelatin form, or chewable tablet. Selection of the excipients and the most appropriate methods for formulation in view of the particular purpose of the composition is within the scope of ordinary persons skilled in the art. For example, drops, solutions, syrups and suspensions may be more appropriate for administration of the betaine compound directly to infants, while powder, tablets and capsules may be more appropriate for administration of the betaine compound to the breast-feeding mother. In general, pharmaceutical compositions and dietary supplements for oral administration are preferred.

Further embodiments of the second aspect of the invention provide the composition comprising an effective amount of betaine compound together with edible acceptable excipients and/or carriers for use as defined above, wherein the composition is an edible product. In a particular embodiment, the composition is an edible infant product. In another embodiment, the edible composition is an infant formula.

The examples below demonstrate that higher betaine ingestion during lactation decreased adiposity and improved systemic metabolism later in life. Without wanting to be bound by theory, the inventors think that betaine-induced improvements in offspring metabolic health may be mediated by modulation of the infant's intestinal microbiota. This theory is supported by obtained evidence related to betaine's ability to promote growth of certain beneficial gut bacterial communities and by disrupting of betaine's effects by continued antibiotic treatment.

The intestinal microbiota plays an important role in heath and disease. It exerts important metabolic activities by extracting energy from otherwise indigestible dietary polysaccharides such as resistant starch and dietary fibres. These metabolic activities also lead to the production of important nutrients, such as short-chain fatty acids (SCFA), vitamins (e.g. vitamin K, vitamin B12 and folic acid) and amino acids, which humans are unable to produce for themselves. In addition, the intestinal microbiota participates in the defence against pathogens by mechanisms such as colonisation resistance and production of antimicrobial compounds. Furthermore, the intestinal microbiota is involved in the development, maturation and maintenance of the gastrointestinal sensory and motoric functions, the intestinal barrier and the mucosal immune system. There is growing evidence that dysbiosis of the gut microbiota is associated with the pathogenesis of both intestinal and extra-intestinal disorders. "Dysbiosis" is a term for imbalance or maladaptation of intestinal microbiota.

The beneficial modulation of the intestinal microbiota afforded by betaine supplementation may thus result in additional benefits. The present disclosure also refers to a betaine compound for use in the beneficial modulation of intestinal microbiota. Beneficial modulation is understood as enhancing growth of beneficial intestinal microbial communities. The present description also refers to a betaine compound for use in prevention and/or treatment of disorders associated to dysbiosis of intestinal microbiota in a subject, wherein the prevention and/or treatment comprises administering the betaine compound directly to the subject during infancy or, alternatively, to the subject's mother during breast-feeding. This can be reformulated as use of a betaine compound for the preparation of a composition for the prevention and/or treatment of disorders associated to dysbiosis of intestinal microbiota in a subject, wherein the composition is administered directly to the subject during infancy or, alternatively, to the subject's mother during breast-feeding. The disclosure also relates to a method for the prevention and/or treatment of disorders associated to dysbiosis of intestinal microbiota comprising administering directly to a subject during infancy or, alternatively, to the subject's mother during breast-feeding an effective amount of a betaine compound, together with pharmaceutically or edible acceptable excipients and/or carriers. Said disorders include undernourishment, infections, inflammatory bowel disease, irritable bowel syndrome (IBS), coeliac disease, allergy, asthma, as well as obesity and associated disorders such as cardiovascular diseases, insulin resistance, type 2 diabetes; hypertension, sleep apnoea, respiratory problems, dyslipidaemia and cancer.

Figure 4:
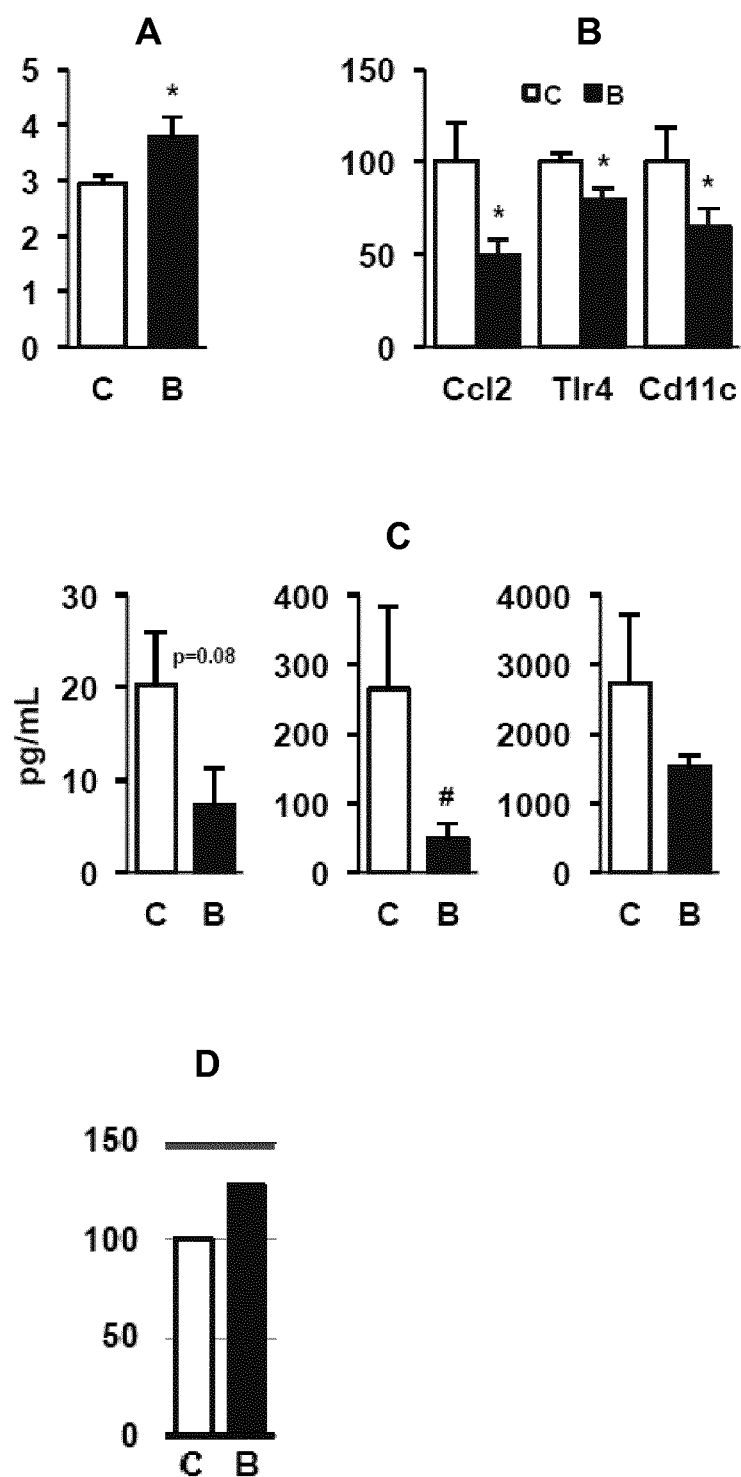
FIG. 4: A) Goblet cell number expressed as goblet cells/ 100 µm in ileum sections at 6 weeks of life (n=16/group). B) Relative expression of mRNA of inflammatory markers Ccl2m Tlr4 and Cd11c in eWAT from 6-week-old male mice (n=8-10/group). C) Circulating levels of inflammatory markers MCP1, IL-6 and Pai-1 expressed in pg/mL from 6-week-old male mice (n=10/group). D) Relative ileal mRNA levels of Muc2 at 6 weeks of life (n=8/group). Data are mean±sem. *, t-test p<0.05; #, Mann-Whitney U test p<0.05. For all figures: white bars represent control mice (C, n=10) and black bars represent betaine-treated mice (B, n=10).

In the context of the benefits afforded by betaine supplementation the inventors have also found that betaine promotes intestinal barrier integrity (see example 2.4 and FIG. 4). The present disclosure also refers to a betaine compound for use in maintaining or ameliorating intestinal barrier function in a subject, wherein the maintaining or ameliorating intestinal barrier function comprises administering the betaine compound directly to the subject during infancy or, alternatively, to the subject's mother during breast-feeding. This can be reformulated as use of a betaine compound for the preparation of a composition for maintaining or ameliorating intestinal barrier function in a subject, wherein the composition is administered directly to the subject during infancy or, alternatively, to the subject's mother during breast-feeding. The disclosure also relates to a method for maintaining or ameliorating intestinal barrier function in a subject comprising administering directly to the subject during infancy or, alternatively, to the subject's mother during breast-feeding an effective amount of a betaine compound, together with pharmaceutically or edible acceptable excipients and/or carriers. In a particular embodiment the subject is a human. In another particular embodiment the subject is an animal.

Infant undernourishment results in intestinal dysbiosis and impaired intestinal barrier function, which has multiple consequences for the child, including nutrient malabsorption, impaired growth and cognitive development, bacteria translocation (endotoxemia) and systemic inflammation. This can have critical consequences, from stunting to peritonitis. Therefore, ameliorating or maintaining the intestinal barrier function in undernourished infants could potentially affect the absorption and metabolism of amino acids, proteins, lipids, carbohydrates, and other nutrients.

Maintenance or improvement of the intestinal barrier function not only contributes to improve offspring's metabolic health, but has further benefits, particularly, in preventing endotoxemia and infections. This is especially relevant for infants at risk of suffering frequent infections, such as undernourished infants.

The present disclosure further relates to a betaine compound for use in preventing infections in a subject, wherein the prevention comprises administering the betaine compound directly to the subject during infancy or, alternatively, to the subject's mother during breast-feeding. This can be reformulated as use of a betaine compound for the preparation of a composition for the prevention of infections in a subject, wherein the composition is administered directly to the subject during infancy or, alternatively, to the subject's mother during breast-feeding. The disclosure also relates to a method preventing infections in a subject comprising administering directly to the subject during infancy or, alternatively, to the subject's mother during breast-feeding an effective amount of a betaine compound, together with pharmaceutically or edible acceptable excipients and/or carriers. In a particular embodiment the subject is a human. In another particular embodiment the subject is an animal.

All embodiments described above for the prevention of obesity, excessive fat accumulation and/or metabolic disorders associated with either of the foregoing also apply to the prevention and/or treatment of disorders associated to dysbiosis of intestinal microbiota, to maintaining or ameliorating intestinal barrier function, and to preventing infections. The betaine compound is, as defined above, preferably selected from glycine betaine, arsenobetaine, proline betaine, 4-hydroxyproline betaine and tryptophan betaine, more preferably from glycine betaine, arsenobetaine and proline betaine, still more preferably it is glycine betaine.

As disclosed above, the betaine compound may be administered to the infant through the breast milk, i.e. by feeding betaine compound to the subject's mother during breast-feeding, or, alternatively, it may be administered directly to the subject during infancy, for example as a dietary supplement or included in infant formula or infant food. The daily dose of betaine compound to be administered directly to the infant in order to obtain the above benefits may be from 2 to 500 mg/Kg/day, in particular from 4 to 100 mg/Kg/day, more particularly from 4 to 50 mg/Kg/day. When the betaine compound is administered to the subject's mother, the daily dose may from 500 mg to 20 g per day, in particular from 1 to 10 g/day, more particularly from 2 to 6 g/day The effective daily dose of betaine compound according to the present disclosure may be administered by directly ingesting pure betaine compound, for example in the form of a powder to be ingested directly or dissolved in liquids. However, the present disclosure is also related to a composition comprising an effective amount of betaine compound together with one or more pharmaceutically or edible acceptable excipients and/or carriers for use in the prevention and/or treatment of disorders associated to dysbiosis of intestinal microbiota, to maintaining or ameliorating intestinal barrier function and to preventing infections, as defined above. The composition may be a pharmaceutical composition with pharmaceutically acceptable excipients and/or carriers or, alternatively, a dietary supplement with edible acceptable excipients and/or carriers or, alternatively, an edible product with edible acceptable excipients and/or carriers. When the composition is an edible product it may be, for example, an infant formula.

When considering the prevention of infections, the infections are in particular gut infections, for example, infections causing gastroenteritis, such as enteropathogens. Further, the prevention of infections, preferably gut infections, may comprise prevention during infancy and/or childhood. The present disclosure also contemplates that the subjects may be subjects at risk of suffering from infections, particularly because of suffering from undernutrition and/or because of being subject of antibiotic treatments.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Betaine in all examples is glycine betaine.
1. Materials and Methods
1.1. Human Study Design Briefly, exclusively breastfeeding mothers and infants arrived between 8:00-10:00 am on the campus of the University of Oklahoma Health Sciences (Oklahoma City, Okla., USA). The mother was encouraged to empty the entire breast using a hospital grade breast pump. Our main outcome variable for the present study was weight-for-length z score (WLZ) at 1 month of age, adjusted for birth WLZ (and other co-variates). This is algebraically identical to the difference in WLZ between birth and 1 month of life adjusted for birth WLZ, and thus reflects the change in WLZ during the first month of life.

1.2. Milk Metabolomics Analysis

One-carbon metabolites s-adenosylmethionine (SAM), s-adenosylhomocysteine (SAH), methionine, cystathionine, choline, and betaine, were determined by LC-MS/MS as previously described (M. Inoue-Choi, et al, One-carbon metabolism nutrient status and plasma s-adenosylmethionine concentrations in middle-aged and older Chinese in Singapore. Int J Mol Epidemiol Genet 3, 160-173 (2012)). 5-methyltetrahydrofolate was measured by LC-MS/MS as previously described (E. Arning, et al, Quantitation of 5-methyltetrahydrofolate in cerebrospinal fluid using liquid chromatography-electrospray tandem mass spectrometry. Methods Mol Biol 1378, 175-182 (2016)). Total homocysteine was measured by LC-MS/MS. For this analysis samples were prepared by adding 10 μL of breast milk or standards to 120 μL of internal standard solution (containing d4-homocysteine in 4 mM of dithiothreitol dissolved in distilled water). After incubation at room temperature for 30 min, samples were deproteinized with 200 μL acetonitrile and 0.1% formic acid, and centrifuged at 1400 rpm for 5 minutes. Samples were analyzed following injection of 10 μL of extract on a Synergi Hydro 4μ 150×3 mm (Phenomenex), maintained at 30° C., and eluted in a gradient with buffer A (100% water, 0.5% formic acid and 0.25% heptafluorobutyric acid) and buffer B (100% acetonitrile, 0.5% formic acid 0.25% heptafluorobutyric acid). Flow rate was 0.5 mL/min, with a step-wise gradient over a total run time of 10 min. Mass Spectrometry was performed on a 4000 QTrap (Sciex, Framingham, Mass.) and the observed (m/z) values of the fragment ions were homocysteine (m/z 136→90) and d4-homocysteine (m/z 140→94). All data were collected and processed using Analyst software v1.4.2 (Sciex, Framingham, Mass.).

1.3. Animal Care and Treatments

All animal protocols were approved by the Institutional Animal Care and Use Committee of the University of Barcelona (Spain). Mice were housed on a 12-hour light-dark cycle with free access to food and water. Male and female ICR-CD1 mice (Envigo) were mated to obtain progeny. To minimize growth variability, litters were adjusted to 8 pups per dam at birth removing heaviest and lightest mice. Glycine betaine (1% wt/vol), ampicilin (1 g/L), and neomycin (0.5 g/L) (Sigma-Aldrich) were administered in water during lactation. After weaning, mice were housed 4 per cage and fed the 2014 Teklad diet (Envigo). For diet-induced obesity, a high-fat diet (HFD, 45% kcal from fat) was provided (D12451, Research Diets). For maternal obesity studies, 6-week-old females were fed HFD for 8 weeks before mating; this same diet was maintained through pregnancy and lactation. To assess milk intake, pups were separated from dams for 2 hours and returned to their cages for 1 hour; difference in body weight before and after the feeding was expressed as grams per initial body weight per hour. For milk harvesting, samples were collected manually under anesthesia (pentobarbital, 40 mg/kg) at day 14 after birth; dams and pups were sacrificed after milk collection, and cecal content obtained for microbiome studies. Body composition was determined by using a 7.0T Bruker Biospect MRI system (Bruker Medical Gmbh, Germany). Indirect calorimetry was measured in metabolic cages (PhenoMaster/LabMaster, TSE Systems GmbH, Germany); $O_2$, $CO_2$, food intake, and locomotor activity were monitored for 48 hours, and data analyzed using 2-way ANOVA for repeated measures. Intraperitoneal glucose (1.5 g/kg) and insulin (0.6 U/kg) tolerance test were performed after a 16 or 4 hour fast, respectively. Mice were anesthetized (intraperitoneal pentobarbital, 50 mg/kg) and sacrificed between 9-11 am.

1.4. Biochemical Analyses

Mouse milk samples were diluted 1:3 before macronutrient analysis by mid-infrared spectroscopy in a Miris Analyzer (Miris AB). Relative betaine concentrations were determined by liquid chromatography (Acquity UPLC BEH HILIC column, Waters) coupled to mass spectrometry (QqQ/MS 6490, Agilent). Plasma insulin was determined by ELISA (Millipore). Plasma MCP-1, IL-6 and PAI-1 were measured using Milliplex Map (EMD Millipore, Merck). Hepatic and fecal triglycerides were quantified in chloroform-methanol extracts from liver or feces (50 mg) using Triglyceride Assay Kit (Sigma-Aldrich).

1.5. Gene Expression Analysis

Total RNA from tissues was isolated with TRI Reagent (Sigma-Aldrich) and cDNA obtained with High-capacity cDNA kit (Applied Biosystems). qPCR was performed with SybrGreen (Takara Bio), using Hprt as housekeeping gene. Primer sequences are the following:

```
Ccl2 forward:
                                        (SEQ ID NO: 1)
5'-CAAGATGATCCCAATGAGTAG-3'

Ccl2 reverse:
                                        (SEQ ID NO: 2)
5'-TTGGTGACAAAAACTACAGC-3'

Tlr4 forward:
                                        (SEQ ID NO: 3)
5'-GCCTCCCTGGCTCCTGGCTA-3'

Tlr4 reverse:
                                        (SEQ ID NO: 4)
5'-CAGGGACTTTGCTGAGTTTCTGATCCA-3'

Cd11c forward:
                                        (SEQ ID NO: 5)
5'-AGTCTGTTGGGTTCTGTAAG-3'

Cd11c reverse:
                                        (SEQ ID NO: 6)
5'-ACAGTTCTGTTATGACATGC-3'

Hprt forward:
                                        (SEQ ID NO: 7)
5'-GCCCCAAAATGGTTAAGGTTG-3'

Hprt reverse:
                                        (SEQ ID NO: 8)
5'-GTCAAGGGCATATCCAACAAC-3'
```

-continued

Muc2 forward:
(SEQ ID NO: 9)
5'-CTGACCAAGAGCGAACACAA-3'

Muc2 reverse:
(SEQ ID NO: 10)
5'-CATGACTGGAAGCAACTGGA-3'

1.6. Histological Analysis

Tissues were fixed by immersion in formalin, paraffin-embedded, and sections stained with hematoxylin/eosin. For WAT, adipocyte area was measured in 30 random microscopic fields per animal (10-20 cells/field). For ileum, cross-sectional cuts were stained with Periodic acid-Schiff (PAS) method. Ten villi per mouse from 5-6 sections were analyzed. Goblet cell number per villus was determined and expressed as number of cells per 100 μm. Analyses were performed using ImageJ by a researcher blinded to sample ID.

1.7. Gut Microbiome Analysis

Cecal content from 2 and 6-week-old male mice from lean control and betaine-treated dams was collected and stored at −80° C. until bacterial DNA was isolated using the Power-Soil® DNA Isolation Kit (MOBIO Laboratories). Microbial composition was analyzed using Illumina MiSeq System to sequence the V3-V4 region of the 16S rRNA gene. Paired-end reads were processed with QIIME v1.9 and assigned to phylum, class, order, family, genus and species levels. Within-sample diversity was estimated at a rarefaction depth of 4827 reads per sample, and phylogenetic diversity expressed as a function of sequence depth. Unweighted UniFrac distances were used to perform the principal coordinate analysis (PCoA). Differences in relative abundance were determined using LEfSe (N. Segata, et al, Metagenomic biomarker discovery and explanation. Genome Biol 12, R60 (2011)).

1.8. Statistical Analysis

Unless otherwise stated, data are presented as mean±sem. Human milk metabolite data were log-transformed and multivariate regression implemented in SPSS 19.0 (Armonk, N.Y.: IBM Corp.). Two-tailed t-test, Mann-Whitney U test for non-normal distributed data, or one-way ANOVA with Tukey's post-hoc test for more than two groups, were applied to determine statistical significance. P<0.05 was considered significant for all analyses.

2. Results 2.1. Breast Milk Betaine Levels are Inversely Associated with Infant Early Growth in Humans To determine whether milk one-carbon metabolites were associated with maternal overweight and infant growth, 34 mother-infant dyads were studied across a range of maternal BMI (18.5-47.2 kg/m²), who were exclusively breastfed (Table 1). Maternal overweight or obesity (OWO) resulted in higher infant weight-for-length z score (WLZ), fat mass, and lean mass at 1 month compared to normal weight (NW) mothers (Table 1).

TABLE 1

Demographic and metabolic characteristics of participants.

|  | All n = 34 | NW n = 15 | OWO n = 19 | P val[a] |
|---|---|---|---|---|
| MOTHER |  |  |  |  |
| Age (years) | 29.1 (5.1) | 27.7 (5.5) | 30.1 (4.7) | 0.182 |
| Pre-pregnancy BMI (kg/m²) | 27.3 (7.1) | 21.6 (1.8) | 31.8 (6.4) | <0.001 |

TABLE 1-continued

Demographic and metabolic characteristics of participants.

|  | All n = 34 | NW n = 15 | OWO n = 19 | P val[a] |
|---|---|---|---|---|
| INFANT |  |  |  |  |
| Birth |  |  |  |  |
| Gender (female/male) | 19/15 | 9/6 | 10/9 | 0.668 |
| Gestational age (weeks) | 39.6 (1.2) | 39.4 (1.1) | 39.8 (1.2) | 0.295 |
| Weight (kg) | 3.53 (0.48) | 3.39 (0.51) | 3.64 (0.45) | 0.148 |
| Length (cm) | 51.6 (2.3) | 51.6 (2.3) | 51.6 (2.3) | 0.989 |
| WLZ | −0.59 (1.20) | −1.07 (1.30) | −0.21 (1.00) | 0.035 |
| 1 month |  |  |  |  |
| Weight (kg) | 4.67 (0.71) | 4.45 (0.63) | 4.84 (0.73) | 0.115 |
| Length (cm) | 55.8 (2.1) | 55.8 (2.1) | 55.8 (2.2) | 0.955 |
| WLZ | −0.36 (1.04) | −0.87 (0.91) | 0.05 (0.98) | 0.008 |
| Head circumference (cm) | 38.3 (1.3) | 38.4 (1.4) | 38.2 (1.3) | 0.676 |
| DXA-fat mass (%) | 24.1 (2.8) | 22.9 (3.0) | 25.0 (2.4) | 0.027 |
| DXA-fat mass (kg) | 1.19 (0.29) | 1.06 (0.27) | 1.30 (0.26) | 0.013 |
| DXA-lean mass (kg) | 3.64 (0.50) | 3.45 (0.46) | 3.78 (0.48) | 0.050 |
| BREAST MILK |  |  |  |  |
| Choline (μmol/L) | 96.8 (49.0) | 96.3 (61.4) | 97.1 (38.2) | 0.541 |
| Betaine (μmol/L) | 3.12 (2.65) | 3.34 (3.30) | 2.95 (2.09) | 0.951 |
| Methionine (μmol/L) | 4.39 (2.69) | 4.70 (3.51) | 4.15 (1.89) | 0.732 |
| SAM (nmol/L) | 1469 (436) | 1427 (483) | 1503 (406) | 0.542 |
| SAH (nmol/L) | 216 (81) | 201 (83) | 227 (80) | 0.279 |
| Cystathionine (nmol/L) | 44.9 (34.3) | 44.0 (35.4) | 45.7 (34.3) | 0.896 |
| 5-methyl-tetrahydrofolate (nmol/L) | 29.5 (15.9) | 27.0 (16.5) | 31.5 (15.6) | 0.420 |
| Homocysteine (nmol/L) | 207 (68) | 215 (55) | 201 (77) | 0.529 |

Values represent mean (SD). Bold font indicates p < 0.05. [a] Two-tailed t-test between NW and OWO groups for continuous variables; Pearson chi-square test for categorical variables (gender). NW, normal weight; OWO, overweight or obese; WLZ, weight-for-length z-score.

Milk samples at 1 month after birth were analysed to quantify choline, betaine, methionine, SAM, SAH, cystathionine, 5-methyltetrahydrofolate (5-MTHF), and total homocysteine (tHcy), and found significant correlations among metabolites. A categorical comparison between NW and OWO mothers revealed no differences in milk metabolite levels (Table 1). We next examined potential associations between milk analytes and infant WLZ. Among all metabolites, betaine was the only variable significantly correlated to WLZ at 1 month of life (r=−0.40, p=0.018), with only a trend observed for SAH and cystathionine (Table 2).

TABLE 2

Multivariate correlations between milk metabolites and infant WLZ at 1 month of life.

| | All Subjects | | | | Normal Weight | | | |
|---|---|---|---|---|---|---|---|---|
| | Unadjusted | | Adjusted[a] | | Unadjusted | | Adjusted[a] | |
| | r | p val | βstd | p val | r | p val | βstd | p val |
| CHO | −0.09 | 0.593 | −0.07 | 0.666 | 0.01 | 0.981 | 0.05 | 0.890 |
| BET | −0.40 | 0.018 | −0.37 | 0.041 | −0.09 | 0.759 | 0.07 | 0.904 |
| MET | 0.08 | 0.649 | 0.15 | 0.441 | 0.16 | 0.557 | 0.11 | 0.760 |
| SAM | 0.04 | 0.822 | −0.06 | 0.755 | −0.10 | 0.716 | 0.16 | 0.720 |
| SAH | −0.29 | 0.094 | −0.31 | 0.068 | −0.14 | 0.609 | 0.07 | 0.854 |
| CYSTA | −0.34 | 0.050 | −0.33 | 0.062 | −0.34 | 0.216 | −0.15 | 0.693 |
| 5-MTHF | 0.13 | 0.449 | 0.10 | 0.568 | 0.32 | 0.248 | 0.17 | 0.614 |
| tHCY | −0.00 | 0.996 | 0.09 | 0.629 | 0.13 | 0.643 | 0.15 | 0.650 |

| | Overweight and Obese | | | |
|---|---|---|---|---|
| | Unadjusted | | Adjusted[a] | |
| | r | p val | βstd | p val |
| CHO | −0.35 | 0.142 | −0.38 | 0.200 |
| BET | −0.78 | <0.001 | −0.80 | <0.001 |
| MET | 0.09 | 0.718 | 0.18 | 0.664 |
| SAM | 0.07 | 0.772 | 0.09 | 0.776 |
| SAH | −0.66 | 0.002 | −0.83 | 0.001 |
| CYSTA | −0.43 | 0.070 | −0.64 | 0.042 |
| 5-MTHF | −0.21 | 0.394 | −0.18 | 0.577 |
| tHCY | 0.05 | 0.836 | 0.08 | 0.797 |

Metabolite levels were log-transformed and the correlation to 1-month WLZ was assessed.
Bold font indicates p < 0.05.
βstd, standardized beta coefficient from regression model; CHO, choline; BET, betaine; MET, methionine; SAM, s-adenosylmethionine; SAH, s-adenosylhomocysteine; CYSTA, cystathionine; 5-MTHF, 5-methyl-tetrahydrofolate; tHCY, total homocysteine.
[a]Model adjusted for maternal age, pre-pregnacy BMI, gestational age, and birth WLZ.

Adjustment for maternal age, pre-pregnancy BMI, gestational age, and birth WLZ did not substantially modify the unadjusted estimates ($\beta_{std}$=−0.37, p=0.041, Table 2). The correlation between betaine and WLZ was particularly strong in infants from OWO mothers ($\beta_{std}$=−0.80, p<0.001), while no association was observed in NW mothers ($\beta_{std}$=0.07, p=0.904; Table 2). A similar obesity-dependent effect was observed for SAH (Table 2). Milk betaine content also correlated to other growth parameters, including ponderal index, and no correlation was observed to head circumference or body composition measures (data not shown).

Altogether, these results indicate that infants born to mothers with obesity but exposed to higher milk betaine content showed decreased growth at 1 month, compared to infants with lower betaine exposure.

2.2. Dietary Betaine Transfers into Breast Milk and Decreases Offspring Adiposity in Mice To study whether milk betaine modulates growth and obesity risk, we performed maternal supplementation experiments in mice exclusively during lactation. Dams were randomly assigned to control (C) or treatment (B, 1% betaine in water) groups the first day after delivery. Milk samples were collected at day 14 after birth from a subset of dams to determine betaine levels. Supplementation increased milk betaine content by 5-fold (p<0.0001, FIG. 1A) without altering macronutrient composition or energy content (FIGS. 1B-2C). Fourteen-day-old offspring showed increased plasma betaine (1.8-fold, p<0.05, FIG. 1D). Supplementation did not modulate offspring growth patterns during lactation (FIG. 1E) or milk intake (FIG. 1F). However, body composition analysis at 6 weeks of age revealed decreased fat mass in betaine-treated compared to control male mice (p<0.05, FIG. 2A). Other metabolic parameters including glucose tolerance, food intake, energy expenditure, respiratory exchange ratio, and activity levels did not differ between groups in young mice (data not shown).

To test whether betaine interacts with maternal obesity, betaine supplementation was performed during lactation in a mouse model of maternal obesity. Dams were fed a high-fat diet (HFD) for 8 weeks before mating, and randomly assigned to control (MO-C) or betaine treatment (MO-B) groups at delivery. Supplementation was performed as described above. Maternal obesity resulted in increased offspring weight gain during lactation, as compared with offspring of lean mothers (compare FIGS. 1E and 2B). In this context, betaine supplementation moderated offspring growth compared to controls (FIG. 2B) with no differences in milk intake (FIG. 2C), and induced a trend towards lower fat mass at 6 weeks of age (FIG. 2D).

Maternal betaine-induced changes in young mice translated into long-term metabolic effects in male offspring, and also protected against diet-induced obesity in both male and female mice. These data indicate that increased betaine exposure during early life might suffice for lowering adiposity. Treatment also protected against hepatic lipid accumulation after high-fat feeding.

Figure 3:
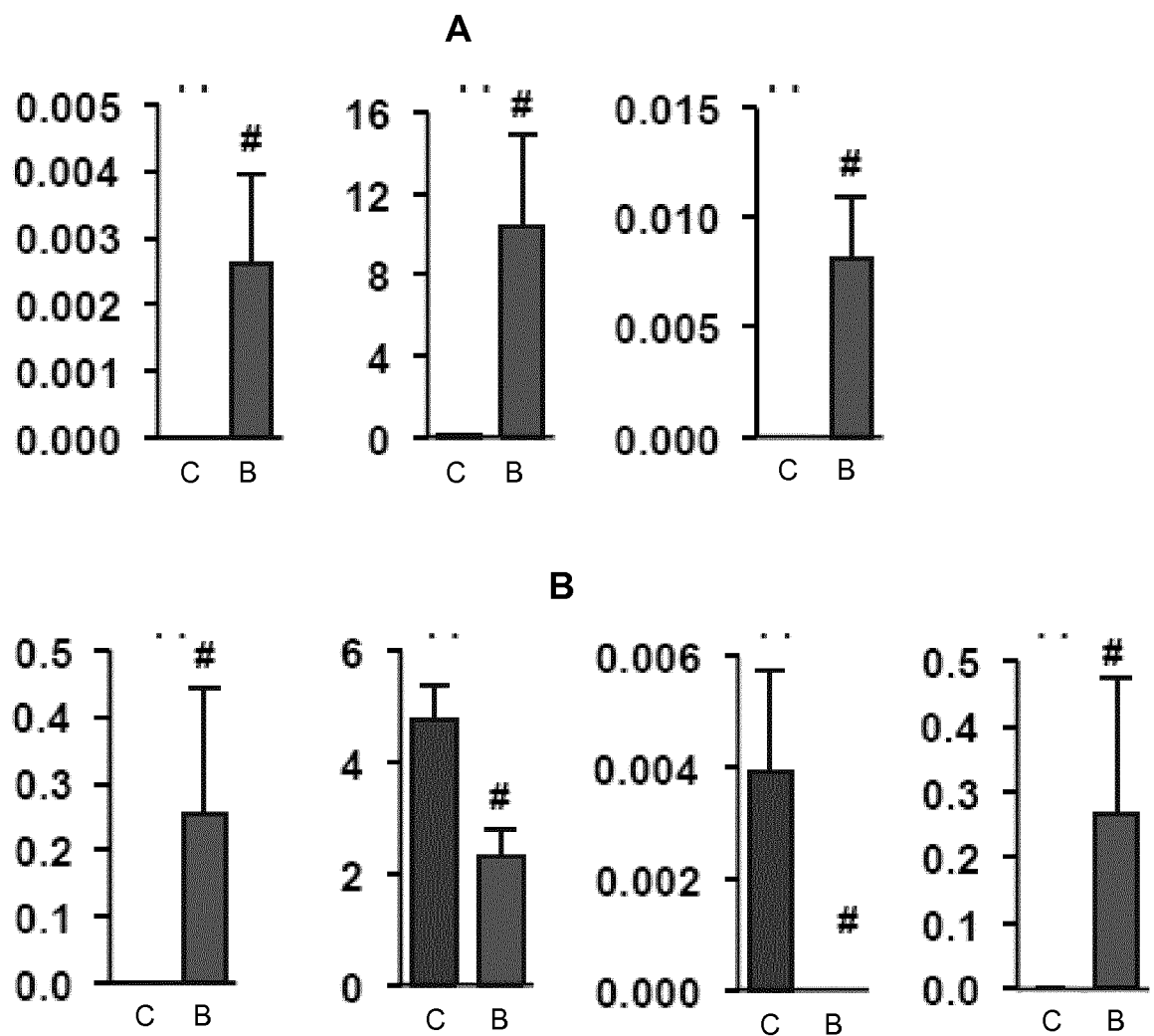
FIG. 3. Relative abundance (%) of differentially enriched genus identified by LEfSe in male offspring of betaine-treated (B, n=10) or control dams (C, n=10) at 2 weeks of age (A) and 6 weeks of age (B).

2.3. Maternal Betaine Supplementation Modulates Offspring Early-Life Gut Microbiota Since the intestinal microbiome is influenced by postnatal nutrition, it was considered whether microbiome alterations may mediate betaine's effects. Cecal content from 2- and 6-week-old male mice from lean control and betaine-treated dams were analysed. To account for inter-litter variability, 8 and 6 litters per group at 2 and 6 weeks of life were analysed, respectively. Principal coordinate analysis of unweighted UniFrac distances showed that maternal betaine modulated microbial community composition at 2 weeks of age, with no differences observed at 6 weeks. Phylogenetic diversity did not differ between groups. Linear discriminant analysis effect size (LEfSe) analysis identified several bacterial groups that significantly differed between groups, including *Actinobacteria* spp., *Akkermansia* spp., and *Pseudomonas* spp. at 2 weeks, and *Akkermansia* spp., *Odoribacter* spp., *Oscillospiraceae* spp., and *Roseburia* spp. at 6 weeks (FIG. 3A-3B). Among these bacterial groups, only differences in *Akkermansia* spp. levels sustained a more stringent bioinformatic analysis by trimming very low-abundance sequence reads before LEfSe.

*Roseburia* spp. are known butyrate producers, which can induce beneficial metabolic effects in the host. Notably, *Akkermansia muciniphila* was the only species altered at both 2 and 6 weeks of age, and the only bacterial group that sustained a more stringent bioinformatic analysis. A number of studies have reported an association between *Akkermansia muciniphila* and improved metabolic health. Interestingly, increased *Akkermansia* spp. population has been recently associated with slower weight gain in a mouse model of postnatal undernutrition. Furthermore, *Akkermansia muciniphila* prior studies demonstrate that administration to adult mice increases ileal goblet cell number and improves the gut barrier function, leading to decreased systemic inflammation and ameliorated metabolic health.

No differences in cecal short-chain fatty acid were found at 6 weeks of age. Moreover, betaine supplementation did not modify the maternal intestinal microbiome.

2.4. Maternal Betaine Supplementation Improves Intestinal Epithelium Function, Low-Grade Systemic Inflammation, and Metabolic Dysfunction.

Six-week-old offspring from betaine-treated dams showed no differences in ileal villi length, but had increased goblet cell number (1.3-fold, $p<0.05$, FIG. 4A) and Muc2 mRNA expression (FIG. 4D). These changes were accompanied by decreased mRNA levels of inflammatory markers (Ccl2, Tlr4, Cd11c) in epididymal white adipose tissue (eWAT, FIG. 4B). Expression of Ccl2 (or monocyte chemoattractant protein 1, MCP-1) was also decreased in brown adipose, liver, and skeletal muscle. Moreover, supplementation decreased circulating levels of pro-inflammatory marker interleukin-6 (IL-6, $p<0.05$), while MCP-1 and plasminogen activator inhibitor-1 (PAI-1) only showed a numerical decrease ($p=0.08$ and $p=0.25$, respectively, FIG. 4C).

2.5. Maternal Betaine Supplementation Improves Offspring Metabolic Health Throughout Adulthood.

Figure 5:
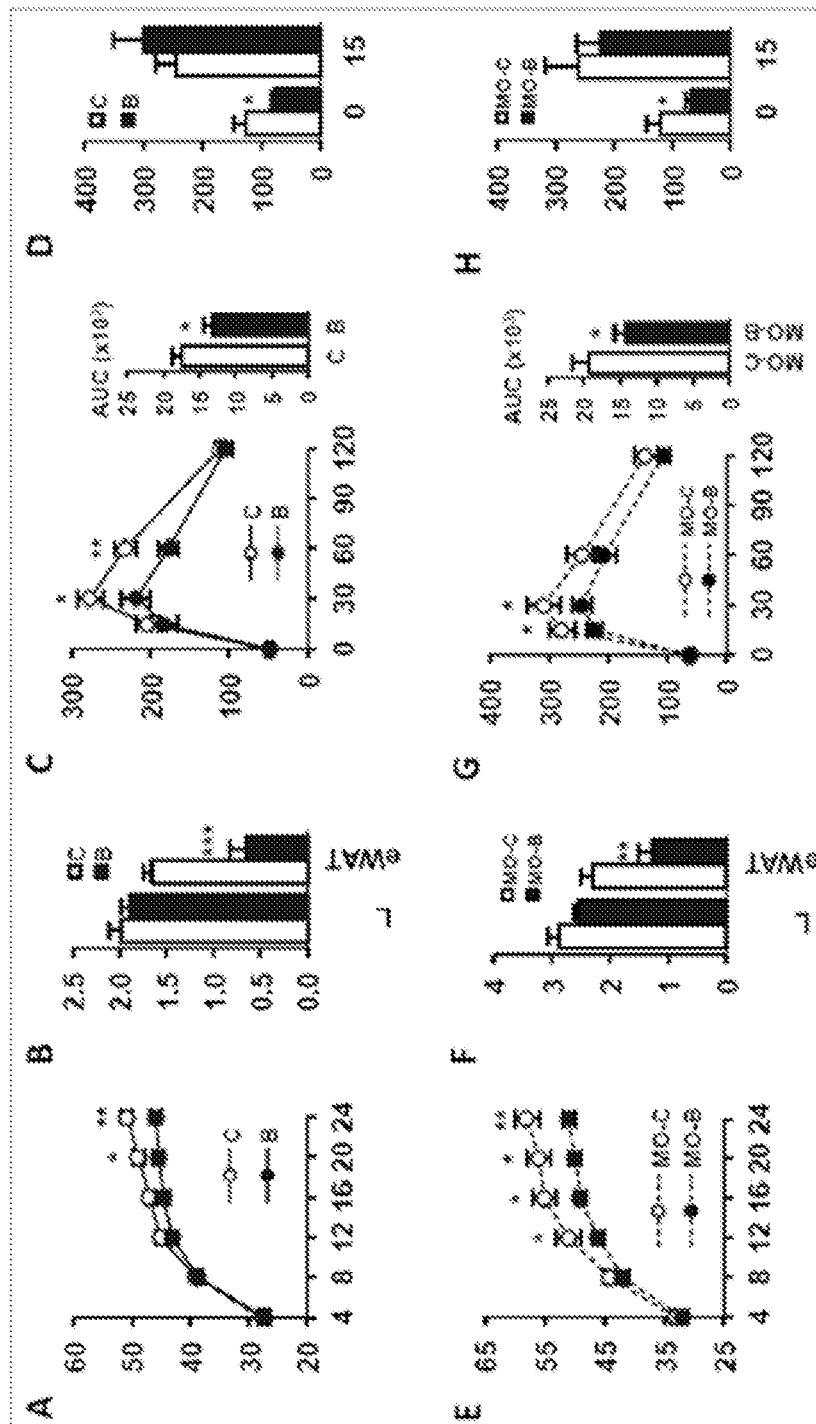
FIG. 5: A) Male offspring from control (white bars/ circles, n=16) or betaine-treated dams (black bars/circles, n=16) were fed a chow diet after weaning and body weight (expressed in g; Y axis) was monitored until 24 weeks of age (weeks of age in the X axis). B) Liver (L) and eWAT weight expressed in g after sacrifice; Y axis represents tissue weight in g. C) Glucose tolerance at week 20; Y axis represents glucose concentration in mg/dL; X axis represents time in minutes. D) Insulin levels at times 0 and 15 minutes after glucose load; Y axis represents insulin concentration in pmol/L. E) Male offspring from obese control (MO-C, n=1) and betaine-treated (MO-B, n=13) dams were maintained on a chow diet after weaning and body weight (expressed in g; Y axis) was monitored until 24 weeks of age (weeks of age in the X axis). F) Liver (L) and eWAT weight after sacrifice; Y axis represents tissue weight in g. G) Glucose tolerance at week 20; Y axis represents glucose concentration in mg/dL; X axis represents time in minutes. H) Insulin levels at times 0 and 15 minutes after glucose load; Y axis represents insulin concentration in pmol/L. Data are mean±sem. *, t-test p<0.05; , p<0.01; *, p<0.001.

It was also investigated whether the above changes during early life translated into long-term metabolic improvements. Offspring was maintained on a chow diet after weaning and monitored up to 24 weeks of age. Male mice born to betaine-treated dams showed lower body weight gain throughout adulthood and decreased eWAT weight (FIGS. 5A-B), but no effect was observed in females. Consistent with lower adiposity, adipocyte size and inflammatory markers were decreased in male offspring from betaine-treated dams. Male mice showed a notable improvement in glucose tolerance (FIG. 5C), with no effect in female offspring. Furthermore, basal insulin levels decreased by 40% in treatment compared to control group ($p<0.05$, FIG. 5D). Insulin tolerance testing revealed significantly lower blood glucose at each time point in males from the treatment group, but no difference in the response to insulin administration. Supplementation had no significant effect on hepatic triglyceride accumulation. A similar phenotype was observed in the maternal obesity mouse model, in which adult male offspring showed lower body weight and adiposity (FIGS. 5E-4F), improved glucose tolerance (FIG. 5G), and decreased basal insulin levels (FIG. 5H) in the betaine-treated compared to the control group.

Figure 6:
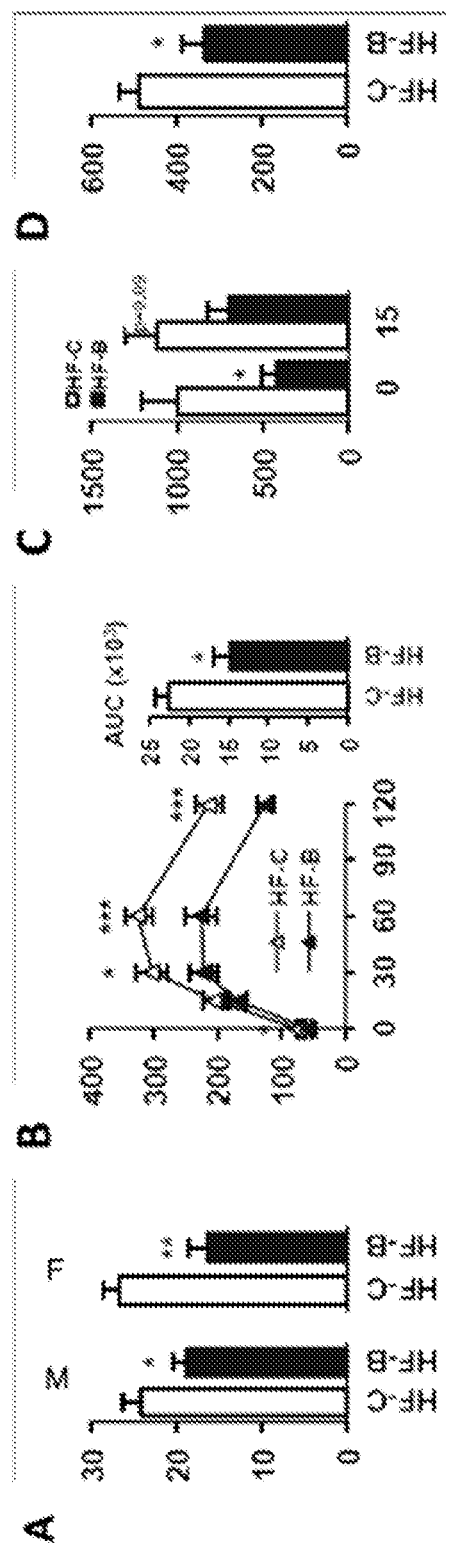
FIG. 6: A) Six-week-old mice born to control (white bars/circles) and betaine-treated dams (black bars/circles) were fed a HFD for 4 months (males (M): n=14 and n=20 for HF-C and HF-B; females (F): n=14/group); body weight gain (expressed in g; Y axis) during high-fat feeding was calculated. B) Glucose tolerance in male mice at 18 weeks of life; Y axis represents glucose concentration in mg/dL; X axis represents time in minutes. C) insulin levels in male mice at 18 weeks of life at times 0 and 15 minutes after glucose load; Y axis represents insulin concentration in pmol/L. D) Hepatic triglyceride levels in male mice (n=8/group); Y axis represents µg TAG/mg protein. Data are mean±sem. *, t-test p<0.05; , p<0.01; *, p<0.001.

It was then tested whether this early-life intervention protected against diet-induced obesity. To this end, 6-week-old offspring of lean control or betaine-treated dams were fed a HFD for 16 weeks (HF-C and HF-B groups, respectively). When challenged with a HFD, both male and female offspring from the betaine-treated group showed lower body weight gain compared to the control group (FIG. 6A). We observed a modest numerical decrease in cumulative food intake, which did not reach statistical significance, and no differences in fecal lipid content. Supplementation ameliorated glucose tolerance (FIG. 6B), and decreased fasting glucose (Time 0, FIG. 6B) and insulin levels (FIG. 6C). Hepatic triglyceride accumulation was reduced by 30% in the HF-B group ($p<0.05$, FIG. 6D).

Figure 7:
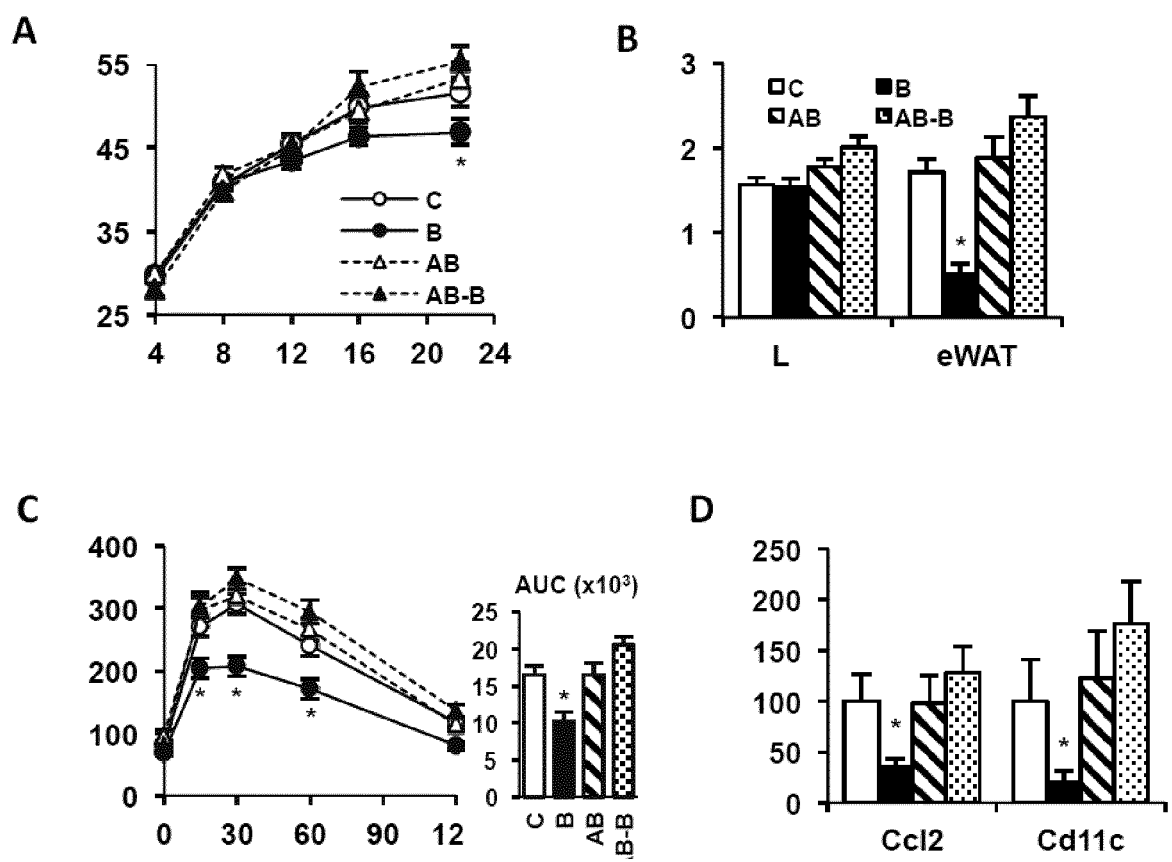
FIG. 7: Male offspring from dams treated with betaine (B group, black circles/bars), antibiotics (AB group, white triangles/hatched bars), antibiotics and betaine (AB-B group, black triangle/dotted bars), or no supplement (C group, white circles/bars) were analyzed (n=12 from 3 litters/group). A) Body weigh was monitored up to 24 weeks of age; Y axis represents body weight in g; X axis represents age in weeks. B) Liver (L) and eWAT depot weight after sacrifice; Y axis represents tissue weight in g. C) Glucose tolerance at 22 weeks of age; Y axis represents glucose concentration in mg/dL; X axis represents time in minutes. D) Relative expression of mRNA of inflammatory markers Ccl2m and Cd11c in eWAT (n=8-12/group). Data are mean±sem. *, one-way ANOVA with post-hoc Tukey test p<0.05 compared to controls.

2.6. Antibiotic Co-Administration During Lactation Blunts Betaine's Long-Term Metabolic Effects Maternal antibiotic administration during early life disrupts offspring gut microbiota composition. It had been previously observed that maternal ampicillin and neomycin administration increases cecum weight and decreases cecal bacterial content in 2-week-old offspring. To test whether the early-life intestinal microbiome contributes to betaine's long-term beneficial metabolic effects, dams were randomly assigned to four groups receiving either betaine (B group), antibiotics (AB group, 1 g/L ampicillin and 0.5 g/L neomycin in the drinking water), antibiotics and betaine (AB-B group), or no supplements (C group), starting the first day after delivery. Offspring was monitored until adulthood. Antibiotic treatment completely abolished long-term betaine-induced effects on body weight (FIG. 7A) and adipose depot weight, while liver weight was not affected by either treatment (FIG. 7B). Furthermore, glucose tolerance was no longer improved by maternal betaine treatment in the presence of antibiotics (FIG. 7C). Similarly, eWAT inflammatory markers were not decreased by betaine in the presence of antibiotics (FIG. 7D).

CITATION LIST

Non Patent Literature

M. Inoue-Choi, et al, One-carbon metabolism nutrient status and plasma s-adenosylmethionine concentrations in middle-aged and older chinese in singapore. Int J Mol Epidemiol Genet 3, 160-173 (2012).

E. Arning, et al, Quantitation of 5-methyltetrahydrofolate in cerebrospinal fluid using liquid chromatography-electrospray tandem mass spectrometry. Methods Mol Biol 1378, 175-182 (2016).

N. Segata, et al, Metagenomic biomarker discovery and explanation. Genome Biol 12, R60 (2011).

The invention claimed is:

1. A method for lowering the risk of obesity, excessive fat accumulation, and/or metabolic disorders in a subject at risk of suffering from any of the foregoing, said method comprising;

administering an effective amount of a betaine compound directly to the subject during infancy or, alternatively, to the subject's mother during breast-feeding of the subject during infancy, wherein, when the betaine compound is administered directly to the subject, said subject has an obese mother, an overweight mother, a diabetic mother, or a mother that smokes.

2. The method according to claim 1, wherein the betaine compound is administered to the subject's mother during breast-feeding of the subject during infancy.

3. The method according to claim 2, wherein the amount of betaine compound administered to the mother is from 1 to 10 g/day.

4. The method according to claim 1, wherein the amount of betaine compound administered directly to the subject during infancy is from 4 to 100 mg/Kg/day.

5. The method according to claim 1, wherein the betaine compound has the formula (I):

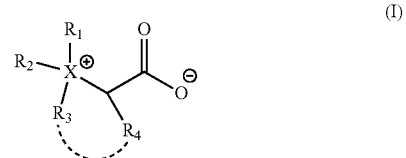

wherein:
X is N or As;
$R_1$ and $R_2$ are independently (C1-C6)alkyl optionally substituted with one or more halogen atoms; and
$R_3$ and $R_4$ form a 5- to 6-membered ring together with the atoms to which they are attached, and wherein said 5- to 6-membered ring is optionally substituted with one or more substituents selected from the group consisting of OH, halogen, and (C1-C3)alkyl, and wherein (C1-C3)alkyl is optionally substituted with one or more halogen atoms; or alternatively
$R_3$ is (C1-C6)alkyl; and
$R_4$ is H or (1H-indol-3-yl)methyl.

6. The method according to claim 1, wherein the betaine compound is glycine betaine.

7. The method according to claim 1, which is for lowering the risk of suffering from obesity.

8. The method according to claim 1, wherein the betaine compound is administered in the form of a composition comprising an effective amount of a betaine compound and a pharmaceutically acceptable or edible excipient.

9. The method according to claim 8, wherein said composition is an infant formula.

10. The method according to claim 8, wherein said composition is a dietary supplement.

11. A method for lowering the risk of obesity, excessive fat accumulation, and/or metabolic disorders in a subject at risk of suffering from any of the foregoing, said method comprising:
administering an effective amount of a betaine compound directly to the subject during infancy or, alternatively, to the subject's mother during breast-feeding of the subject during infancy,
wherein, when the betaine compound is administered directly to the subject, said subject is at risk of suffering from obesity, excessive fat accumulation, and/or metabolic disorders because of excess gestational weight gain, formula feeding, intrauterine growth retardation, or rapid infant grow.

12. The method according to claim 11, wherein the amount of betaine compound administered directly to the subject during infancy is from 4 to 100 mg/Kg/day.

13. The method according to claim 11, wherein the betaine compound has the formula (I):

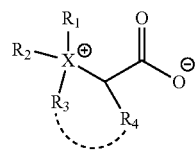

wherein:
X is N or As;
$R_1$ and $R_2$ are independently (C1-C6)alkyl optionally substituted with one or more halogen atoms; and
$R_3$ and $R_4$ form a 5- to 6-membered ring together with the atoms to which they are attached, and wherein said 5- to 6-membered ring is optionally substituted with one or more substituents selected from the group consisting of OH, halogen, and (C1-C3)alkyl, and wherein (C1-C3)alkyl is optionally substituted with one or more halogen atoms; or alternatively
$R_3$ is (C1-C6)alkyl; and
$R_4$ is H or (1H-indol-3-yl)methyl.

14. The method according to claim 11, wherein the betaine compound is glycine betaine.

15. The method according to claim 11, which is for lowering the risk of suffering from obesity.

16. The method according to claim 11, wherein the betaine compound is administered in the form of a composition comprising an effective amount of a betaine compound and a pharmaceutically acceptable or edible excipient.

17. The method according to claim 16, wherein said composition is an infant formula.

18. The method according to claim 16, wherein said composition is a dietary supplement.

19. A method for lowering the risk of suffering from obesity, excessive fat accumulation, and/or metabolic disorders in a subject at risk of suffering from any of the foregoing, said method comprising:
administering an effective amount of a betaine compound directly to the subject during infancy or, alternatively, to the subject's mother during breast-feeding of the subject during infancy,
wherein, when the betaine compound is administered directly to the subject, said subject having received antibiotic treatment.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Ccl2 forward primer

<400> SEQUENCE: 1
caagatgatc ccaatgagta g                                    21

<210> SEQ ID NO 2
<211> LENGTH: 20
<212> TYPE: DNA
<213> ORGANISM: Artificial Sequence
<220> FEATURE:
<223> OTHER INFORMATION: Ccl2 reverse primer

<400> SEQUENCE: 2
ttggtgacaa aaactacagc                                      20

<210> SEQ ID NO 3
<211> LENGTH: 20
<212> TYPE: DNA
<213> ORGANISM: Artificial Sequence
<220> FEATURE:
<223> OTHER INFORMATION: Tlr4 forward primer

<400> SEQUENCE: 3
gcctccctgg ctcctggcta                                      20

<210> SEQ ID NO 4
<211> LENGTH: 27
<212> TYPE: DNA
<213> ORGANISM: Artificial Sequence
<220> FEATURE:
<223> OTHER INFORMATION: Tlr4 reverse primer

<400> SEQUENCE: 4
cagggacttt gctgagtttc tgatcca                              27

<210> SEQ ID NO 5
<211> LENGTH: 20
<212> TYPE: DNA
<213> ORGANISM: Artificial Sequence
<220> FEATURE:
<223> OTHER INFORMATION: Cd11c forward primer

<400> SEQUENCE: 5
agtctgttgg gttctgtaag                                      20

<210> SEQ ID NO 6
<211> LENGTH: 20
<212> TYPE: DNA
<213> ORGANISM: Artificial Sequence
<220> FEATURE:
<223> OTHER INFORMATION: Cd11c reverse primer

<400> SEQUENCE: 6
acagttctgt tatgacatgc                                      20

<210> SEQ ID NO 7
<211> LENGTH: 21
<212> TYPE: DNA
<213> ORGANISM: Artificial Sequence

```
<220> FEATURE:
<223> OTHER INFORMATION: Hprt forward primer

<400> SEQUENCE: 7
gccccaaaat ggttaaggtt g                                            21

<210> SEQ ID NO 8
<211> LENGTH: 21
<212> TYPE: DNA
<213> ORGANISM: Artificial Sequence
<220> FEATURE:
<223> OTHER INFORMATION: Hprt reverse primer

<400> SEQUENCE: 8
gtcaagggca tatccaacaa c                                            21

<210> SEQ ID NO 9
<211> LENGTH: 20
<212> TYPE: DNA
<213> ORGANISM: Artificial Sequence
<220> FEATURE:
<223> OTHER INFORMATION: Muc2 forward primer

<400> SEQUENCE: 9
ctgaccaaga gcgaacacaa                                              20

<210> SEQ ID NO 10
<211> LENGTH: 20
<212> TYPE: DNA
<213> ORGANISM: Artificial Sequence
<220> FEATURE:
<223> OTHER INFORMATION: Muc2 reverse primer

<400> SEQUENCE: 10
catgactgga agcaactgga                                              20
```